United States Patent [19]

Barberet et al.

[11] Patent Number: Plant 5,433

[45] Date of Patent: Apr. 9, 1985

[54] CARNATION NAMED LONKORPI

[75] Inventors: Nicole Barberet; Yves Ducloux, both of Antibes, France

[73] Assignee: Laboratoire de Physiologie Vegetale de La Londe, Antibes, France

[21] Appl. No.: 516,512

[22] Filed: Jul. 25, 1983

[51] Int. Cl.[3] ..... A01H 5/00

[52] U.S. Cl. ..... Plt./70

[58] Field of Search ..... Plt./70

*Primary Examiner*—Robert E. Bagwill

*Attorney, Agent, or Firm*—Charles W. Rummler

[57] ABSTRACT

A new spray carnation variety particularly distinguished by its very light chartreuse yellow blossoms, the petal edges of which are predominately edged with cardinal red. These blossoms are borne on straight, rather rigid peduncles branching from a strong, upright stem having abundant foliage and a vigorous, upright growth habit. This variety is also rather resistant to *Fusarium oxysporum.*

1 Drawing Figure

BACKGROUND OF THE NEW PLANT

Our new spray carnation is the result of breeding efforts carried on by us at La Londe, Les Maures, France, since 1975 with the object of developing a new variety having nice color and good quality of flower stem and plant growth habit, and which would be resistant to *Fusarium oxysporum.* This new plant originated as a seedling produced by our crossing of selected and individually identified plants growing among a stock of spray carnations maintained at La Londe for breeding purposes and this particular seedling was selected by us for propagation and test because of its very unusual distinctive flower coloration. This discovery plant was reproduced by us at La Londe, by means of cuttings, with a very favorable result with respect to retention of the novel characteristics of the parent plant. This caused us to continue asexual propagation through several successive generations and over a period of years, which definitely determined that the novel and distinctive characteristics of the discovery plant are fully retained from generation to generation and appear to be firmly fixed.

DESCRIPTION OF THE DRAWING

Our new spray carnation is illustrated by the accompanying photographic drawing which shows, in full color, the spray portion of a typical flowering stem with buds and flowers in various stages of opening, the colors shown being as nearly true to those specified herein as is reasonably possible to obtain by conventional photographic procedures.

DESCRIPTION OF THE NEW PLANT

The following is a detailed description of our new spray carnation discovery based upon observations of greenhouse grown plants at La Londe, France, in the Spring of 1983, the color designations being specified according to The R.H.S. Colour Chart published by The Royal Horticultural Society of London, England.

THE PLANT

Origin: Seedling

Parentage:

*Seed parent.*—Stock Variety No. 429 B.

*Pollen parent.*—Stock Plant No. 72 M C 1. These unnamed varieties are individually identified in our permanent records and are maintained in our collection of spray carnations for breeding purposes at La Londe, France.

Classification:

*Botanic.*—*Dianthus caryophyllus.*

*Commercial.*—Spray Carnation.

Form: Tall, erect bush with at least four stems emitted near the ground.

Height: Averaging about 100 cm. at eight months.

Main stem:

*Length.*—Less than 15 cm. due to pinching.

Branching character: Very branched from all stems.

Growth habit: Vigorous, upright and rather rigid.

Foliage:

*Quantity.*—Abundant.

*Number of leaves.*—At least 120.

*Leaf size.*—About 13 cm. long and 1 cm. wide, in average at the seventh node.

*Leaf shape.*—Linear with curved margins and acuminate tip.

*Texture.*—Leathery.

*Color.*—Upper side — 189A. Under side — 189A.

*Ribs and veins.*—Hardly noticeable.

*Rachis.*—Hardly noticeable.

THE BUD

Form: Long ovoid.

Size: Medium.

*Diameter.*—About 1.1 cm. in average.

*Length.*—About 3.2 cm. in average.

Rate of opening: Normal for carnations.

Color of petals:

*When sepals first divide.*—Primrose Yellow.

*When petals begin to unfurl.*—A little darker than at full bloom.

Sepals:

*Number.*—Five

*Shape.*—Joined at lower part with upper part of acute form and sharply pointed at the apex. The sepals are hooded over the bud and stand up when the flower opens.

*Color.*—Inside — Greenish white. Outside — 145A.

Calyx:

*Shape.*—Long and generally cylindrical.

*Splitting.*—The calyx does not split.

*Aspect.*—Smooth.

Flower Stem:

*Length.*—About 56 cm.

*Character.*—Erect and rather thin.

*Color.*—189A.

THE FLOWER

Blooming habit: Recurrent, blooming profusely during the midseason of Spring and Fall.

Size of bloom: Small.

*Diameter.*—Averaging about 5.3 cm.

*Depth.*—Averaging about 4.5 cm.

Borne: In cluster.

Shape:

*When bloom first opens.*—High centered.

*When bloom matures.*—Dome-shaped.

Petalage:

*Number of petals.*—Averaging about 28.

*Arrangement.*—Imbricated.

*Form.*—Fan-shaped with flat to slightly wavy margins.

*Texture.*—Soft.

*Appearance.*—Satiny.

Color.—Outer Petal: Body — 2D plus 187C and 53D. Base — Pale greenish yellow. Reverse side — 4D plus 187C and 50C. Inside Petal: Body — 2D plus 187C and 53D. Base — Pale greenish yellow. Reverse side — 4D plus 187C and 50C.

Flower stem:

*Length.*—About 56 cm.

*Character.*—Upright and of good strength.

*Color.*—189A.

Fragrance: Present but light.

Persistence: The flowers hang on and dry.

Lasting quality:

*As a cut flower.*—At least ten days in vase keeping.

Disease resistance: Rather resistant to *Fusarium oxysporum* as observed INRA, Antibes, Alpes-Maritimes, France.

REPRODUCTIVE ORGANS

Stamens:

*Number.*—About 13.

*Arrangement.*—Around the pistils.

*Anthers.*—Size: Less than 4 mm. Color: Whitish. Filaments: Color — Whitish.

Pistils:

*Number.*—Two.

*Styles.*—Color — Whitish.

*Stigmas.*—Color — Light crimson.

Character of ovaries: Globular, light green and hardly ribbed.

This new variety of spray carnation most resembles the variety "MAY BRITT" and is distinguished by having a brighter color and higher earliness than "MAY BRITT".

We claim:

1. A new and distinct variety of spray carnation, substantially as herein shown and described, characterized by the chartreuse yellow coloration of its small blooms, the petals of which are edged with a combination of cardinal red and greyed purple. The flowers of this plant are produced profusely on long, straight and strong flowering stems and the plant has a vigorous and upright growth habit with abundant foliage and resistance to *Fusarium oxysporum*.

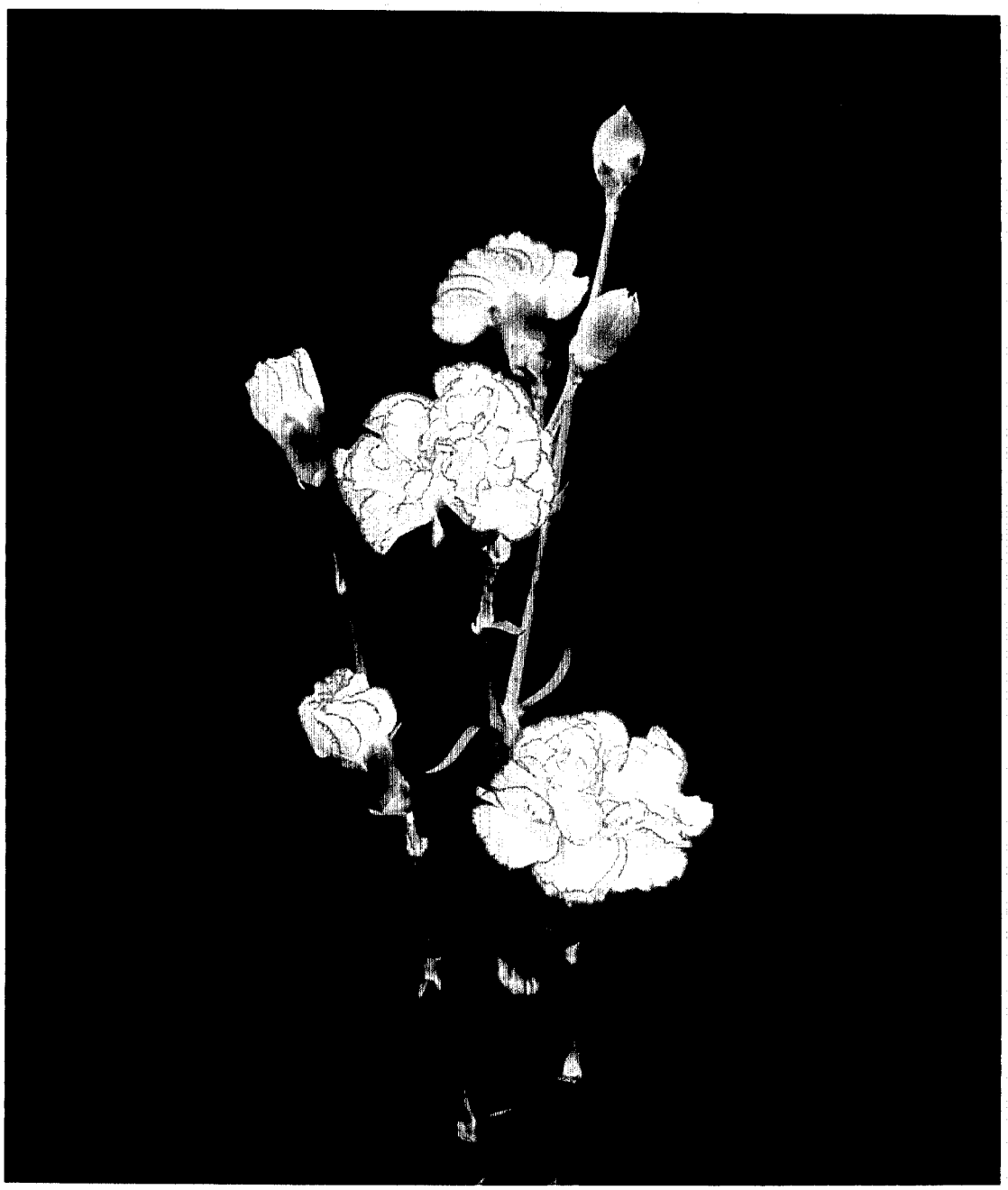

* * * * *